US012755495B2

(12) United States Patent
Hanlon et al.

(10) Patent No.: US 12,755,495 B2
(45) Date of Patent: Oct. 6, 2026

(54) AUGMENTED REALITY SYSTEM WITH IMPROVED REGISTRATION METHODS AND METHODS FOR MULTI-THERAPEUTIC DELIVERIES

(71) Applicant: MEDIVIEW XR, INC., Cleveland, OH (US)

(72) Inventors: Aydan Thomas Hanlon, Akron, OH (US); Jeffrey Harold Yanof, Solon, OH (US); Ross Daniel Hinrichsen, Plymouth, MN (US); Peter Nicholas Braido, Wyoming, MN (US)

(73) Assignee: MEDIVIEW XR, INC., Cleveland, OH (US)

( * ) Notice: Subject to any disclaimer, the term of this patent is extended or adjusted under 35 U.S.C. 154(b) by 91 days.

(21) Appl. No.: 18/674,102

(22) Filed: May 24, 2024

(65) Prior Publication Data

US 2024/0394985 A1 Nov. 28, 2024

Related U.S. Application Data

(60) Provisional application No. 63/504,675, filed on May 26, 2023.

(51) Int. Cl.
*A61B 34/20* (2016.01)
*A61B 90/00* (2016.01)
(Continued)

(52) U.S. Cl.
CPC ............ *G06T 19/006* (2013.01); *A61B 34/20* (2016.02); *A61B 90/37* (2016.02); *G06T 19/20* (2013.01);
(Continued)

(58) Field of Classification Search
CPC ... G06T 19/006; G06T 19/20; G06T 2210/41; G06T 2219/2016; A61B 34/20; A61B 90/37; A61B 2090/365
See application file for complete search history.

(56) References Cited

U.S. PATENT DOCUMENTS 9,498,132 B2 * 11/2016 Maier-Hein .......... A61B 34/10
10,895,906 B2 1/2021 West et al.
(Continued)

OTHER PUBLICATIONS

Written Opinion of the International Searching Authority dated Aug. 19, 2024.

*Primary Examiner* — Xiao M Wu
*Assistant Examiner* — Ryan Allen Barham
(74) *Attorney, Agent, or Firm* — Jacob M. Ward; Ward Law Office LLC

(57) ABSTRACT

Ways to register an anatomical feature of a patient using augmented reality are provided. Included is a system for registration of an anatomical feature of a patient, the system having an imaging system, a tracked instrument, an augmented reality system, and a computer system. The imaging system can be configured to image the patient and generate an imaging dataset. The tracked instrument can be configured to generate a tracked instrument dataset. The augmented reality system can be configured to display an imaging volume hologram in augmented reality. The computer system can be in communication with the augmented reality system, the imaging system, and the tracked instrument. The computer system can generate an imaging volume dataset based on a first axial plane and a second axial plane, can render the imaging volume dataset into the imaging volume hologram, and can project the image volume hologram in an augmented reality.

18 Claims, 10 Drawing Sheets

(51) Int. Cl.
*G06T 19/00* (2011.01)
*G06T 19/20* (2011.01)

(52) U.S. Cl.
CPC ..... *A61B 2090/365* (2016.02); *G06T 2210/41* (2013.01); *G06T 2219/2016* (2013.01)

(56) References Cited

U.S. PATENT DOCUMENTS

| | | | | |
|---|---|---|---|---|
| 11,304,759 | B2 * | 4/2022 | Kovtun | G06T 11/20 |
| 11,701,183 | B2 | 7/2023 | Martin, III et al. | |
| 2004/0225686 | A1 | 11/2004 | Li et al. | |
| 2020/0078948 | A1 | 3/2020 | Krause et al. | |
| 2020/0197107 | A1 | 6/2020 | Ryan et al. | |
| 2020/0405395 | A1 | 12/2020 | Gullotti et al. | |
| 2021/0161612 | A1 | 6/2021 | Black et al. | |
| 2021/0161613 | A1 * | 6/2021 | Poltaretskyi | G06N 3/09 |
| 2021/0236209 | A1 | 8/2021 | Black et al. | |
| 2021/0298836 | A1 | 9/2021 | Black et al. | |
| 2021/0315637 | A1 * | 10/2021 | Ida | A61B 34/10 |
| 2021/0358228 | A1 | 11/2021 | Black et al. | |
| 2022/0117674 | A1 | 4/2022 | Black | |
| 2023/0255692 | A1 * | 8/2023 | Petkov | G06T 19/00<br>606/1 |

* cited by examiner

AUGMENTED REALITY SYSTEM WITH IMPROVED REGISTRATION METHODS AND METHODS FOR MULTI-THERAPEUTIC DELIVERIES

CROSS-REFERENCE TO RELATED APPLICATIONS

This application claims the benefit of U.S. Provisional Application No. 63/504,675, filed on May 26, 2023. The entire disclosure of the above application is incorporated herein by reference.

FIELD

The present technology relates to holographic augmented reality applications and, more particularly, medical applications employing holographic augmented reality.

INTRODUCTION

This section provides background information related to the present disclosure which is not necessarily prior art.

Image-guided surgery has become standard practice for many different procedures. Image-guided surgery can visually correlate intraoperative data with preoperative and postoperative data to aid a practitioner. The use of image-guided surgery has been shown to increase the safety and the success of various surgical procedures. Image-guided surgery can be further enhanced through the use of augmented reality (AR). Use of AR can provide an interactive experience of a real-world environment where one or more features that reside in the real world can be enhanced by computer-generated perceptual information, sometimes across multiple sensory modalities. In a medical setting, AR can be useful for enhancing the real environment in relation to a patient and a surgical theatre. For example, a practitioner can view content-specific information in the same field of view as the patient while performing a medical procedure, without the practitioner having to change their gaze.

There are certain issues, however, that can arise before, during, and/or after an image-guided surgery. For example, the anatomy of a patient is not necessarily static. Various internal movements, such as breathing or the heart beating, can cause a rhythmic shift, for example, in the internal anatomy of a patient. Undesirably, these internal movements may displace a surgical location, which can impair the use of augmented reality during the procedure. This problem can be further exacerbated by the fact that these internal motions are not linear. For example, inflation and deflation can result in significant changes in both lung deformation and volume of air flow at specific phases during the respiratory cycle.

What is more, one of the standard ways of producing a three-dimensional (3D) medical image today is through the use of a computed tomography (CT) scan which produces an image series which can be referred to as a DICOM data set. The DICOM data set can be further processed using software to segment out the structures of the body and to produce 3D images of these structures that can be used for further study or in the use of augmented reality. These DICOM data sets must be painstakingly looked at one at a time and then processed through a method of software segmentation, where each of the structures of interest within each individual scan slice must be outlined and identified.

Alternatively stated, the CT scans produce two dimensional (2D) image slices of varying thickness. The individual 2D segmented DICOM slices then must be reassembled into a 3D model, rendered, and then smoothed. Processing the 2D image slices from the CT scans can include many image transfer and processing steps to produce an anatomical volume suitable to be viewed in augmented reality. Due to the numerosity of steps in this process, and the high cost to acquire and operate a CT scan, this scanning method may be unavailable in certain circumstances. Also, because of how costly CT scans can be, the number of available CT scans can be limited and not readily available to all patients in need thereof. It may also be necessary for a patient to be exposed to an undesired dose of radiation during a CT scan. This exposure to radiation can be harmful for human tissue which puts the patient and caregivers at risk. This radiation exposure may also result in long term negative side effects.

In certain augmented reality systems, current registration techniques can be cumbersome and are not ideal for all surgical applications. Accordingly, there is a continuing need for improved registration techniques for holographic augmented reality systems and their applications.

SUMMARY

In concordance with the instant disclosure, an augmented reality system that can provide a real time bi-plane/multi-view fluoroscopic fusion hologram rendered in proximity to a patient for use during a procedure, has surprisingly been discovered.

The present disclosure provides a system for registration of an anatomical feature of a patient using augmented reality. The system can include an imaging system, a tracked instrument, an augmented reality, and a computer system. The imaging system can be configured to image the anatomical feature of the patient and generate an imaging dataset. The tracked instrument can be configured to generate a tracked instrument dataset. The augmented reality system can be configured to display an imaging volume hologram of the anatomical feature of the patient in augmented reality. The computer system can be in communication with the augmented reality system, the imaging system, and the tracked instrument. The computer system can generate an imaging volume dataset based on a first axial plane and a second axial plane, can render the imaging volume dataset into the imaging volume hologram, and can project the image volume hologram in an augmented reality environment of the augmented reality system.

The present disclosure further provides a method for registration of anatomy of a patient using augmented reality for a procedure on a patient. The method can include providing the system of the present disclosure including an augmented reality system, an imaging system, a tracked instrument, and a computer system. The method can include positioning the tracked instrument in a first axial plane and collecting, from the tracked instrument, the tracked instrument dataset. The method can include a step of positioning the imaging system in a second axial plane and a step of collecting, from the imaging system, the imaging dataset. The method can include identifying an internal landmark of the patient with both the tracked instrument and the imaging system. The first axial plane and the second axial plane can be aligned based on the internal landmark identified. An imaging volume dataset based on the first axial plane and the second axial plane can be generated in 3D coordinates. The method can include a step of registering, by the computer system, the imaging volume dataset with the augmented reality system. The imaging volume dataset can be rendered into an imaging volume hologram and projected, by the augmented reality system, the imaging volume hologram.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

FIG. 1 is a schematic depiction of a system for registration of an anatomical feature of a patient using augmented reality;

FIGS. 2A-2C provide a flowchart depicting a method for registration of anatomy of a patient using augmented reality for a procedure on a patient;

FIG. 3 is a flowchart depicting method steps for utilizing a combination of an anatomical landmark and the sagittal midline of the patient;

FIGS. 4A-4B provide a flowchart depicting method steps for registering and calibrating a surgical robot with the augmented reality system;

DETAILED DESCRIPTION

Figure 1:
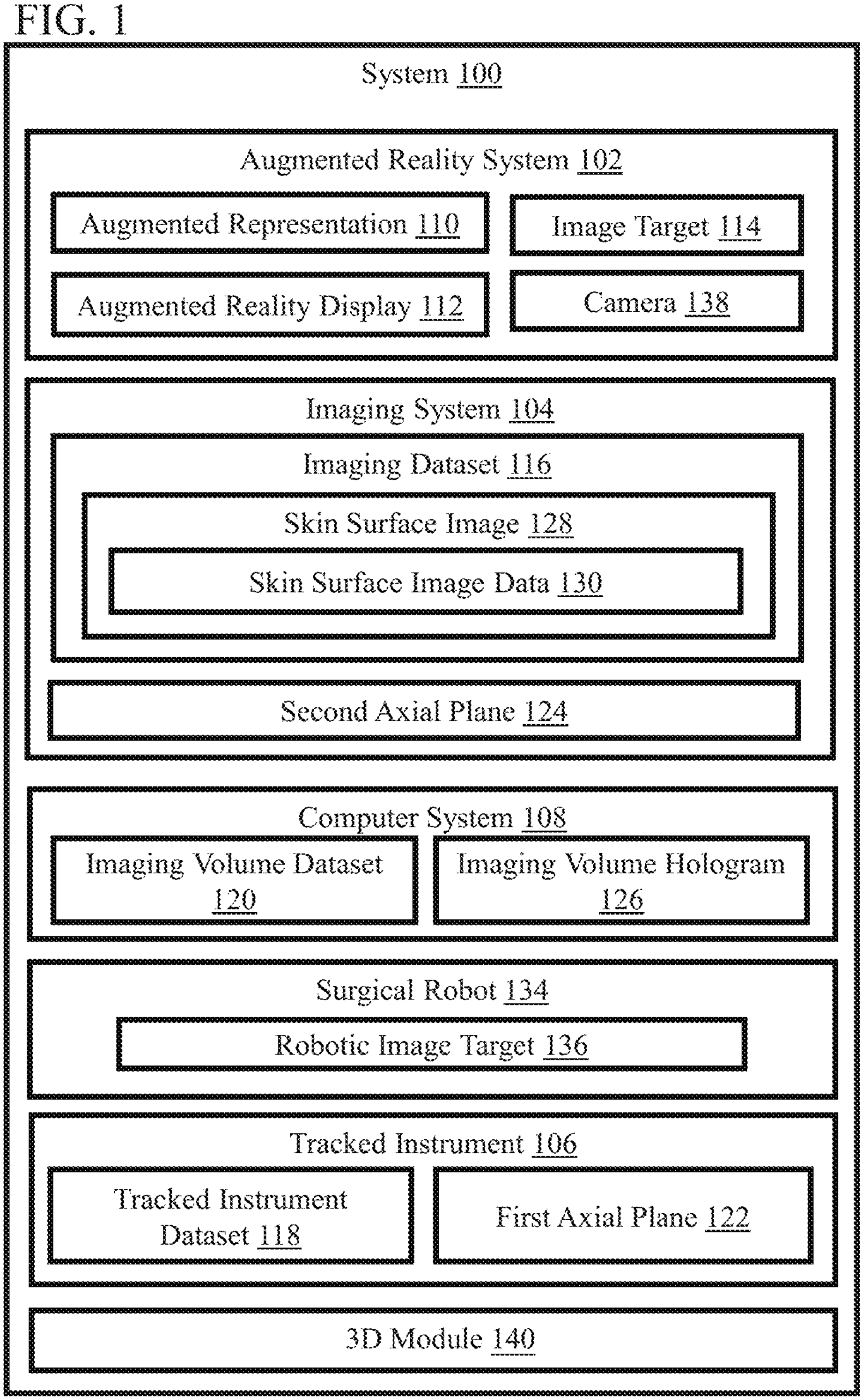

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed, unless expressly stated otherwise. “A” and “an” as used herein indicate “at least one” of the item is present; a plurality of such items may be present, when possible. Except where otherwise expressly indicated, all numerical quantities in this description are to be understood as modified by the word “about” and all geometric and spatial descriptors are to be understood as modified by the word “substantially” in describing the broadest scope of the technology. “About” when applied to numerical values indicates that the calculation or the measurement allows some slight imprecision in the value (with some approach to exactness in the value; approximately or reasonably close to the value; nearly). If, for some reason, the imprecision provided by “about” and/or “substantially” is not otherwise understood in the art with this ordinary meaning, then “about” and/or “substantially” as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term “comprising,” as a synonym of non-restrictive terms such as including, containing, or having, is used herein to describe and claim embodiments of the present technology, embodiments may alternatively be described using more limiting terms such as “consisting of” or “consisting essentially of” Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of “from A to B” or “from about A to about B” is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being “on,” “engaged to,” “connected to,” or “coupled to” another element or layer, it may be directly on, engaged, connected or coupled to the other element or layer, or intervening elements or layers may be present. In contrast, when an element is referred to as being “directly on,” “directly engaged to,” “directly connected to” or “directly coupled to” another element or layer, there may be no intervening elements or layers present. Other words used to describe the relationship between elements should be interpreted in a like fashion (e.g., “between” versus “directly between,” “adjacent” versus “directly adjacent,” etc.). As used herein, the term “and/or” includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

As used herein, the terms "interventional device" or "tracked instrument" refers to a medical instrument used during the medical procedure.

As used herein, the term "tracking system" refers to something used to observe one or more objects undergoing motion and supply a timely ordered sequence of tracking data (e.g., location data, orientation data, or the like) in a tracking coordinate system for further processing. As an example, the tracking system can be an electromagnetic, and optical (e.g., fiber optic) tracking system that can observe an interventional device equipped with a sensor-coil as the interventional device enters, moves through, exits, and while outside of a patient's body.

As used herein, the term "tracking data" refers to information recorded by the tracking system related to an observation of one or more objects undergoing motion.

As used herein, the term "head-mounted device" or "headset" or "HMD" refers to a display device, configured to be worn on the head, that has one or more display optics (including lenses) in front of one or more eyes. These terms may be referred to even more generally by the term "augmented reality system," although it should be appreciated that the term "augmented reality system" is not limited to display devices configured to be worn on the head. In some instances, the head-mounted device can also include a non-transitory memory and a processing unit. An example of a suitable head-mounted device is a Microsoft HoloLens® head-mounted device (Microsoft, Redmond, Washington).

As used herein, the terms "imaging system," "image acquisition apparatus," "image acquisition system" or the like refer to technology that creates a visual representation of the interior of a patient's body. For example, the imaging system can be a computed tomography (CT) system, a fluoroscopy system, positron emission computed tomography, magnetic resonance imaging (MRI) system, an ultrasound (US) system including contrast agents and color flow doppler, or the like.

As used herein, the terms "coordinate system" or "augmented realty system coordinate system" or "augmented reality system coordinates" refer to a 3D Cartesian coordinate system that uses one or more numbers to determine the position of points or other geometric elements unique to the particular augmented reality system or image acquisition system to which it pertains. For example, 3D points in the headset coordinate system can be translated, rotated, scaled, or the like, from a standard 3D Cartesian coordinate system.

As used herein, the terms "image data" or "imaging dataset" or "imaging data" refers to information recorded in 3D by the imaging system related to an observation of the interior of the patient's body. For example, the "image data" or "imaging dataset" can include processed two-dimensional or three-dimensional images or models such as imaging images, e.g., represented by data formatted according to the Digital Imaging and Communications in Medicine (DICOM) standard or other relevant imaging standards.

As used herein, the terms "imaging coordinate system" or "image acquisition system coordinate system" refers to a 3D Cartesian coordinate system that uses one or more numbers to determine the position of points or other geometric elements unique to the particular imaging system. For example, 3D points and vectors in the imaging coordinate system can be translated, rotated, scaled, or the like, to the Augmented Reality system (head mounted displays) 3D Cartesian coordinate system.

As used herein, the terms "hologram", "holographic," "holographic projection", or "holographic representation" refer to a computer-generated image stereoscopically projected through the lenses of a headset. Generally, a hologram can be generated synthetically (in an augmented reality (AR)) and is not a physical entity.

As used herein, the term "physical" refers to something real. Something that is physical is not holographic (or not computer-generated).

As used herein, the term "two-dimensional" or "2D" refers to something represented in two physical dimensions.

As used herein, the term "three-dimensional" or "3D" refers to something represented in three physical dimensions. An element that is "4D" (e.g., 3D plus a time and/or motion dimension) would be encompassed by the definition of three-dimensional or 3D.

As used herein, the term "integrated" can refer to two or more things being linked or coordinated. For example, a coil-sensor can be integrated with an interventional device.

As used herein, the term "real-time" or "near-real time" or "live" refers to the actual time during which a process or event occurs. In other words, a real-time event is done live (within milliseconds so that results are available immediately as feedback). For example, a real-time event can be represented within 100 milliseconds of the event occurring.

As used herein, the terms "subject" and "patient" can be used interchangeably and refer to any vertebrate organism.

As used herein, the term spatial "registration" refers to steps of transforming tracking and imaging dataset associated with virtual representation of tracked devices—including holographic guides, applicators, and ultrasound image stream—and additional body image data for mutual alignment and correspondence of said virtual devices and image data in the head mounted displays coordinate system enabling a stereoscopic holographic projection display of images and information relative to a body of a physical patient during a procedure, for example, as further described in U.S. Patent Application No. 10,895.906 to West et al., and also applicant's co-owned U.S. patent application Ser. No. 17/110,991 to Black et al. and U.S. Patent Application No. 11,701,183 to Martin III et al., the entire disclosures of which are incorporated herein by reference.

The present disclosure relates to a system 100 for registration of anatomy using augmented reality, shown generally in FIG. 1. The system 100 can have an augmented reality system 102, an imaging system 104, a tracked instrument 106, and a computer system 108. The augmented reality system 102 can be configured to display an augmented representation 110 in the form of a hologram. The augmented representation 110 can include a two-dimensional (2D) or a three-dimensional (3D) depiction of relevant information to a medical procedure. Examples of relevant information can include preoperative and/or intraoperative data, such as three-dimensional depictions of an anatomical feature of a patient. The anatomical feature can be the organic matter and/or region of the patient that is the focus of a current procedure. Further examples of the anatomical feature can include organs, portions of organs, tissues, joints, bones, tumors, vasculature, implants, etc. The augmented representation 110 can have many applications and uses such as pre-procedural planning, procedural guidance, and training. It should be appreciated that one skilled in the art can select other information to be depicted for the augmented representation 110. In addition, it should be appreciated that the anatomical or physiological/functional feature can include any portion of the anatomy of the patient.

The augmented reality system 102 can be configured to display the augmented representation 110 via an augmented reality display 112 such as a head mounted display in an augmented reality environment. Desirably, this can allow a practitioner to view the augmented representation 110 in the same field of view as the patient. The augmented reality system 102 can be configured to display an augmented representation 110 over a portion of the patient in an augmented reality environment. The portion of the patient can be the anatomical feature of the patient. Advantageously, this can allow the augmented representation 110 to be depicted directly over the anatomical feature to provide relevant feedback within the context of a position of the anatomical feature. For example, the augmented representation 110 can be an intraoperative scan of the anatomical feature that can be overlaid over the anatomical feature for visualization by the practitioner. In other instances, the portion of the patient can be adjacent to the anatomical feature of the patient. Desirably, this can permit the practitioner to observe the augmented representation 110, while also being able to observe the anatomical feature, within the same field of view.

The augmented representation 110, using the augment reality display 112, can be displayed over an approximated position of the anatomical feature of the patient. For example, the computer system 108 can employ algorithms, machine learning, artificial intelligence, and/or in combination to approximate where the anatomical feature of the patient is according to medically approved tolerances. The computer system 108 can also be manually operated or a hybrid of manual and automatic controls. However, it should be appreciated that the augmented representation 110 can also be displayed on other surfaces and/or augmented representations 110, as desired.

In certain embodiments, the augmented reality system 102 can also include one or more image targets 114 for determining position. The image targets 114 of the augmented reality system 102 can be configured to determine and generate positional data for the augmented reality system 102, such as the approximated position in three-dimensional (3D) space, the orientation, angular velocity, and acceleration of the augmented reality system 102. For example, it should be understood that this can allow holographic imagery to be accurately displayed within the field of view of the practitioner, in operation. Examples of the image targets 114 can include accelerometers, gyroscopes, electromagnetic sensors, and/or optical tracking sensors. It should further be appreciated that a skilled artisan can employ different types and numbers of image targets 114 of the augmented reality system 102, for example, as required by the procedure or situation within which the augmented reality system 102 is being used. It should be appreciated that the system 100 does not require the use of the image target 114 for registration.

The imaging system 104 can be configured to image the anatomical feature of the patient and generate an imaging dataset 116. The imaging dataset 116 can include information and/or media associated with the structure, rotation, and/or position of the anatomical feature in relation to the patient. It should be appreciated that one skilled in the art can select types of data to be included in the imaging dataset 116. Desirably, the imaging system 104 can be utilized to image the anatomical feature of the patient and generate the imaging dataset 116 before a procedure, during a procedure, and/or in combination.

As will be described in further detail below, the imaging dataset 116 can be utilized by the computer system 108 to generate the augmented representation 110. In other words, the imaging system 104 can be used to perform a scan and/or other imaging procedure to generate the imaging dataset 116 to be used to generate the augmented representation 110. For example, the imaging system 104 can include an ultrasound system having at least one active ultrasound probe. The practitioner can move the ultrasound probe over the anatomical feature of the patient to capture the imaging dataset 116, which can include 2D images. The ultrasound probe can be moved along a path along the patient to generate the 2D images. The 2D images can then be transformed by the computer system 108 into the augmented representation 110. Other examples of the imaging system 104 can include computed tomography (CT) systems, electromagnetic systems, cone beam computed tomography (or CBCT) systems, blood gas exchange systems, mechanically controlled ventilation systems, spirometry systems, electrocardiogram (ECG) systems, magnetic resonance imaging (MRI) systems, electromechanical wave propagation systems, transesophageal echocardiogram (TEE) systems, and combinations thereof. However, it should be appreciated that a skilled artisan can employ other imaging procedures and systems for the imaging system 104, within the scope of this disclosure.

The tracked instrument 106 can also be configured to image the anatomical feature of the patient and generate a tracked instrument dataset 118. The tracked instrument dataset 118 can include information and/or media associated with the structure, rotation, and/or position of the anatomical feature in relation to the patient. The tracked instrument 106 can include various instruments, such as a needle, and electromagnetically tracked ultrasound and therefore, the tracked instrument dataset 118 can include ultrasound data. It should be appreciated that the tracked instrument dataset 118 can include an electromagnetic dataset. One skilled in the art can select types of data to be included in the tracked instrument dataset 118. Desirably, the tracked instrument 106 can be utilized to image another anatomical feature of the patient and generate the tracked instrument dataset 118 during the procedure.

The computer system 108 can be configured to generate an imaging volume dataset 120 and to register the imaging volume dataset 120 with the augmented reality system 102. The imaging volume dataset 120 can be generated from the tracking instrument dataset 118 and the imaging dataset 116. As described herein, the tracked instrument 106 can image a first axial plane 122 of the patient to collect the tracked instrument dataset 118 and the imaging system 104 can image a second axial plane 124 to collect the imaging dataset 116. The first axial plane 122 and the second axial plane 124 can be aligned to generate the imaging volume dataset 120 and thereby render and project the imaging volume hologram 126 from the imaging volume dataset 120.

In general, registration can include transforming electromagnetic data from a tracked instrument 106, such as a needle, and electromagnetically tracked ultrasound or the imaging system 104 into the augmented reality system coordinates. Additional imaging data, such as MRI or CT imaging, can also be registered into the augmented reality system coordinates. In certain embodiments, the tracking data for one or more various instruments including imaging devices and imaging data can both be registered to the physical patient thereby registering them with each other. In certain embodiments, additional imaging data can be registered using fiducial sensors placed at one or more locations on a body of a patient.

Figure 2A:
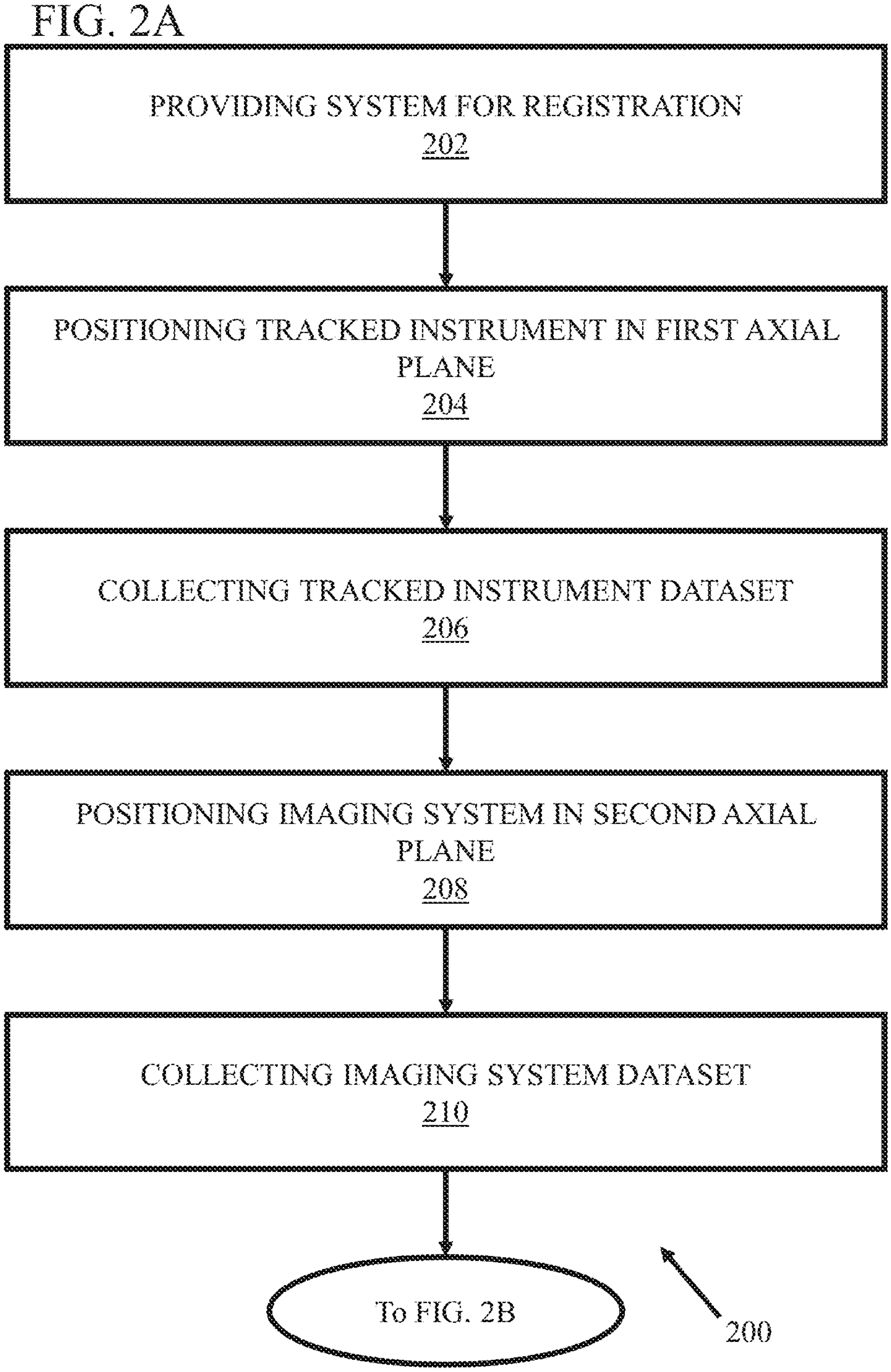
Figure 2B:
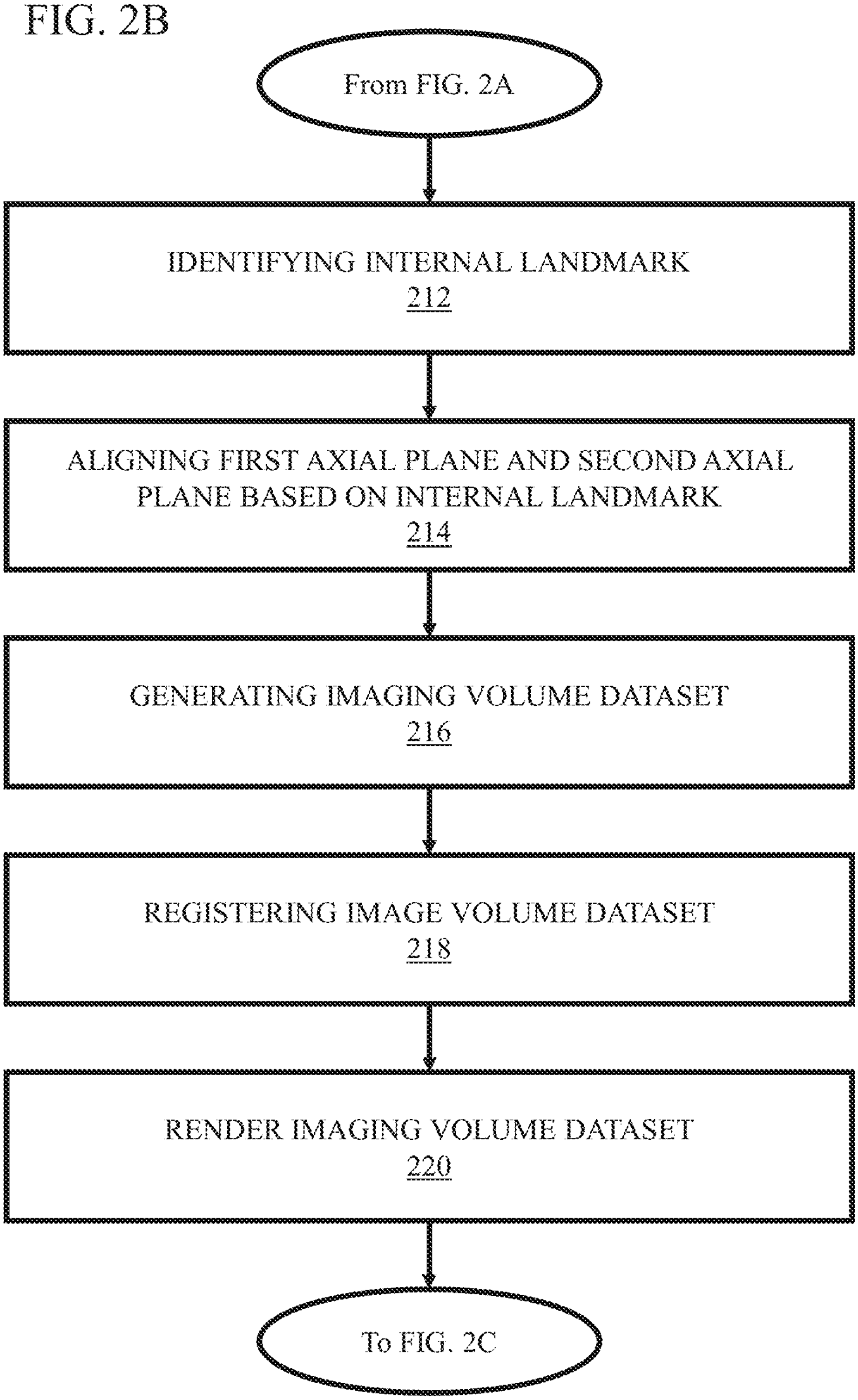
Figure 2C:
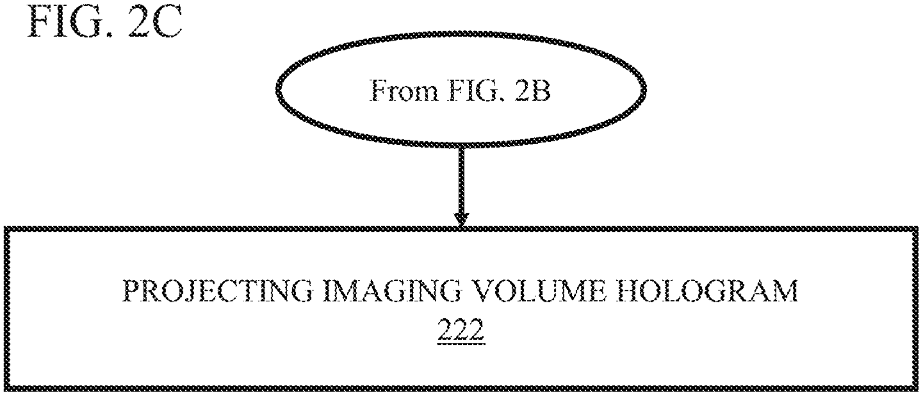

Registration of Imaging System, Tracked Ultrasound and Instruments without Segmentation Instead of, or in conjunction with, segmenting anatomical structures and fiducial markers from datasets, which can involve cumbersome workflow, reconstructed images can be computed in the system 100 based on importing the imaging volume dataset 120. The coordinate system of the reconstructed or reformatted image can be registered to be coplanar and oriented with tracked instrument 106 imaging and used with holographic representation of the tracked instrument 106. With reference now to FIGS. 2A-2C, a method 200 for registration of anatomy of a patient utilizing the positions of the tracked instrument 106 and the imaging system 104 is provided. In this way, the method 200 includes a step 202 of providing a system for registration of anatomy using augmented reality, as described herein. The tracked instrument 106 can be positioned in the first axial plane 122, which corresponds to the patient in a step 204. In a step 206, the tracked instrument 106 can collect the tracked instrument dataset 118 that represents the image shown by the tracked instrument 106, such as an ultrasound probe. The imaging system 104 can be positioned in the second axial plane 124 in a step 208. In a step 210, the imaging system 104 can collect the imaging dataset 116 that represents the image shown via the imaging system 104, such as computed tomography (CT) or magnetic resonance imaging (MRI). While the tracked instrument 106 is held stationary in the second axial plane 124, the corresponding axial image in the imaging dataset can be identified. In an alternative embodiment, the second axial plane 124 of the imaging system 104 can be first selected and the tracked instrument 106 can be navigated to find the tracked instrument 106 image that matches the reference imaging system 104 image.

The method 200 can include a step 212 of identifying a corresponding internal anatomical landmark with both of the imaging system 104 and the tracked instrument 106. In a step 214, the first axial plane and the second axial plane can be aligned based on the anatomical landmark identified. In a step 216, the computer system 108 can generate the imaging volume dataset 120 based on the tracked instrument dataset 118 in the first axial plane 122 and the imaging volume dataset 120 in the second axial plane 124. The imaging volume dataset 120 can be reformatted into orthogonal or oblique images including an image that is reformatted to be coplanar with the tracked instrument image. In a step 218, the computer system 108 can register the imaging volume dataset 120 with the augmented reality system 102. The imaging volume dataset 120 can be used to render, by the computer system 108, to render the imaging volume hologram 126 in a step 220. The method 200 can include a step 222 of projecting the imaging volume hologram 126 with the augmented reality system 102.

Figure 3:
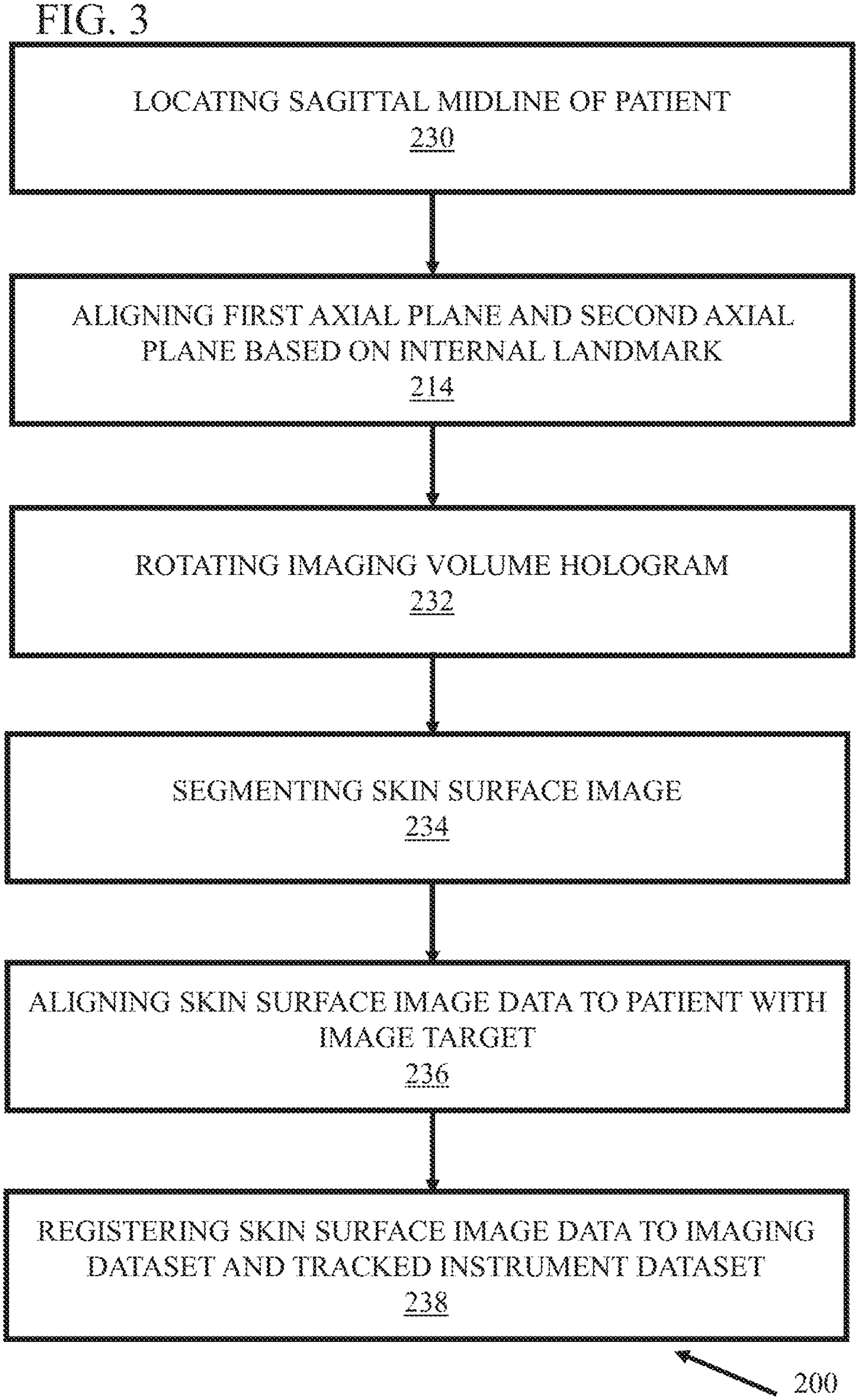

With reference to FIG. 3, certain embodiments include where the method 200 can utilize a combination of an anatomical landmark and the sagittal midline of the patient. In a step 230, the sagittal midline of the patient can be located. Upon positioning the imaging volume hologram 126 such that the physical and holographic anatomical landmarks are congruent in the step 214, the imaging volume hologram 126 can be manually or semi-automatically rotated along the anatomical anterior-posterior axis until the holographic sagittal midline of the imaging volume hologram 126 and physical sagittal midline are congruent in a step 232. This additional alignment can result in a further calibrated registration between the physical patient and the imaging volume hologram 126.

In certain embodiments of the method 200, a step 234 can include automatically segmenting a skin surface image 128 from the imaging dataset 116, thereby creating skin surface imaging data 130. A medical professional can align the skin surface image data 130 to the physical patient using a tracking sensor 132 in augmented reality system coordinates, in a step 236. The tracking sensor 132 can include a 6 degree of freedom (DoF) tracking sensor. The method 200 can include a step 238 of registering the skin surface imaging data 130 to the imaging dataset 116 and the tracked instrument dataset 118 since these are also registered to the physical patient by way of the electromagnetic-to-augmented reality system 102 transformation being performed by locating an image targets and electromagnetic sensor in their respective coordinate systems. It should be appreciated that a localizable camera on the head mounted display of the augmented reality system 102 can used to locate the tracking sensor 132. In this way, the imaging system 104, the tracked instrument 106, and the skin surface of the patient can be registered with each other in augmented reality system coordinates. Subsequent to registration and augmented reality co-projection, methods can be used to militate against occlusion management and depth ambiguity relative to the physical patient. Alternatively, the registered holographic entities can be projected in proximity to the patient, such that the line-of-site does not intersect the holographic projection and the physical target tissue to prevent occlusion and depth ambiguity.

Robotic Integration and Registration for Augmented/Extended Reality (XR) Visualization A multi-arm surgical robot 134 can be used with the system 100 and can be manipulated using hand controls from a display console, which can increase the fine-motor dexterity in manipulation of an endoscopic tool and a surgical instrument via keyhole surgical access. Although the display console can provide 3D information based on virtual or XR, the image content is not intended to facilitate eye-hand (visual motor axis) coordination. Therefore, manipulation of the surgical instrument relative to the endoscopic camera can require extensive training.

Figure 4A:
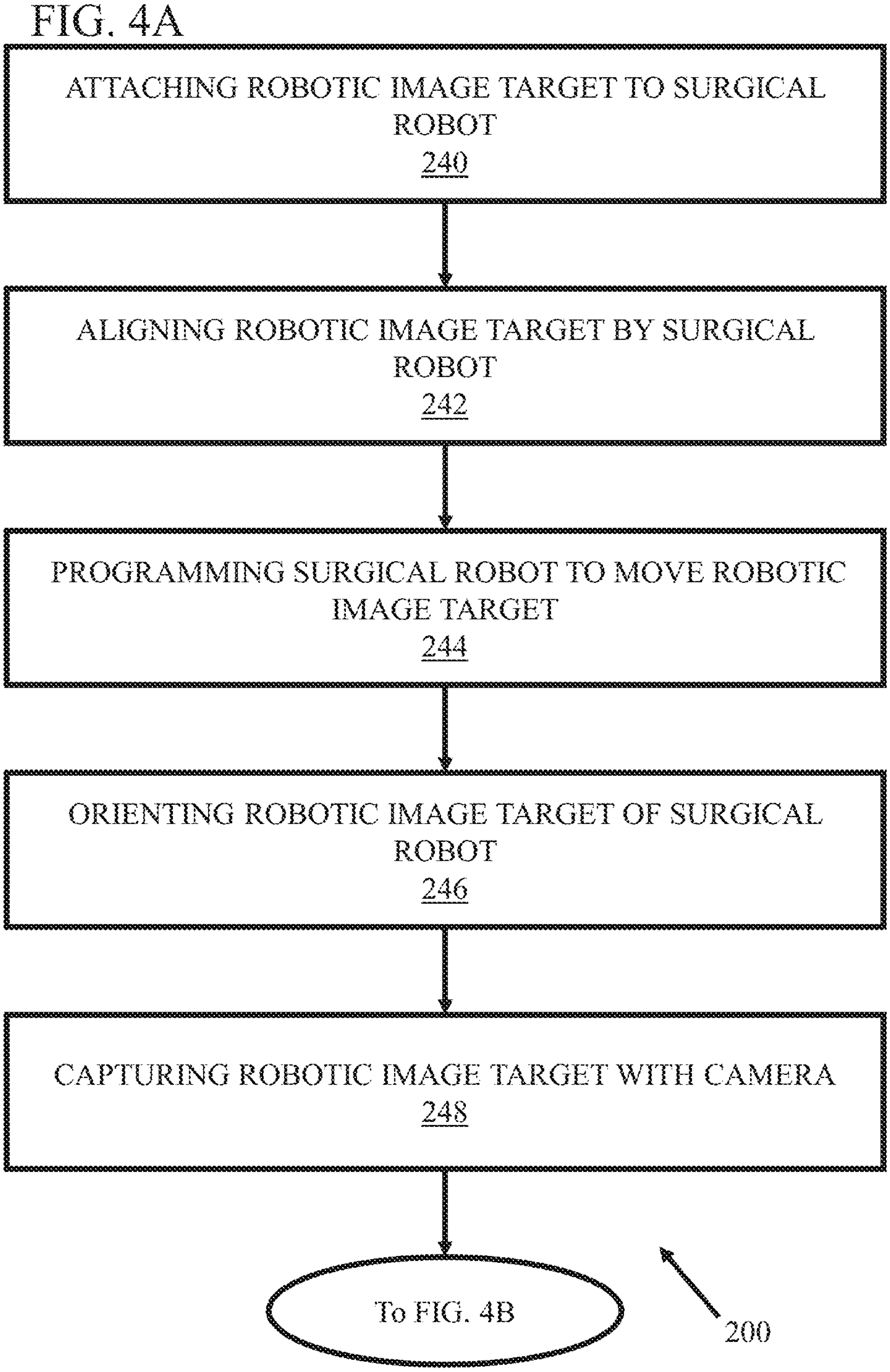
Figure 4B:
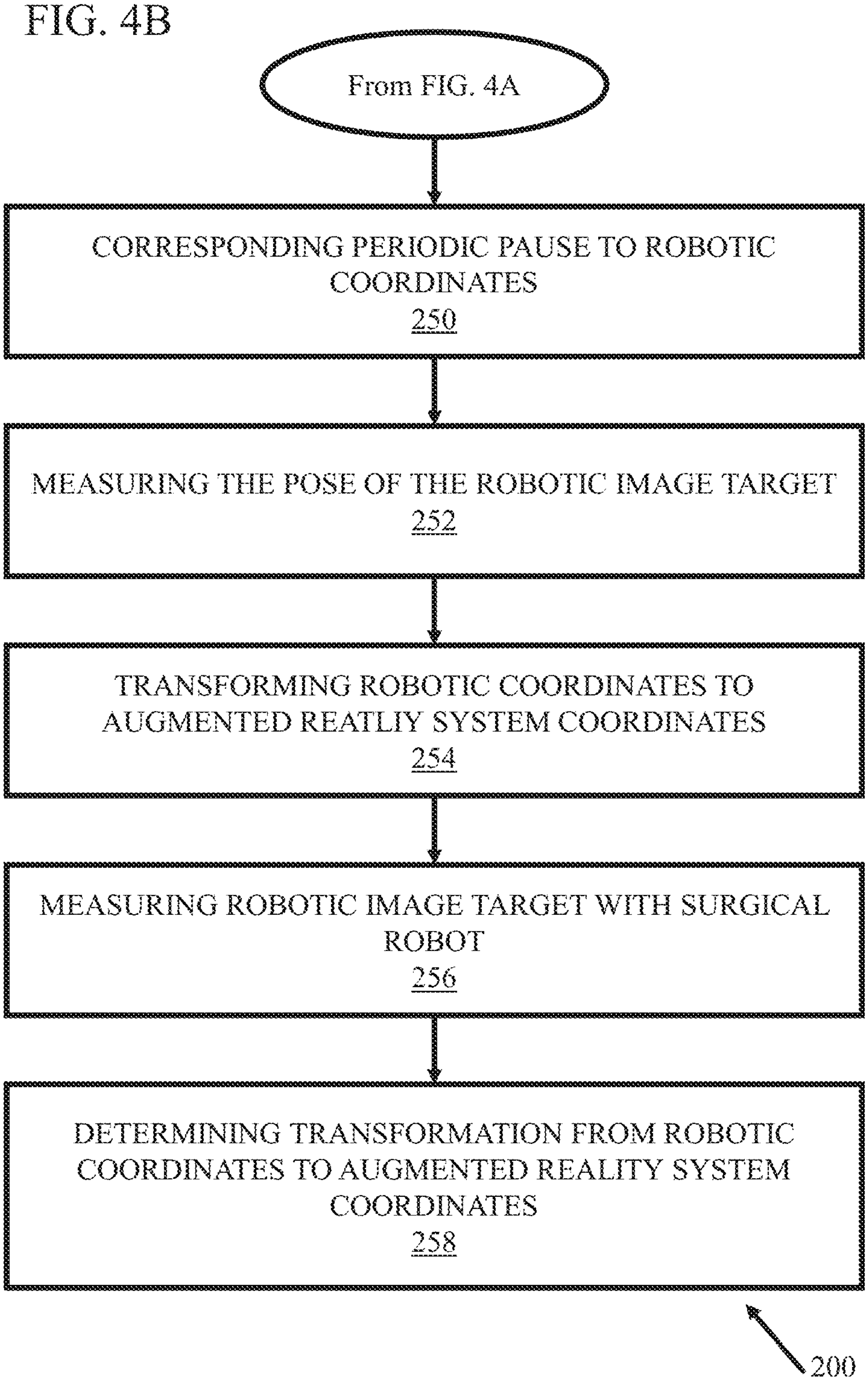

With reference to FIGS. 4A & 4B, in order to register the robotic kinematic chain in the head-mounted display coordinates of the system 100, the method 200 can include a step 240 of attaching a robotic image target 136 to a portion of the surgical robot 134, such as an end-effector, at a predetermined position and a predetermined orientation. The robotic image target 136 can be aligned by the robot system 3D Cartesian coordinate system via a kinematic chain (e.g., mechanically grounded base, shoulder, elbow, forearm, and six-degree of freedom wrist/end-effector) in a step 242. The robotic image target 136 can also be localizable with the augmented reality system coordinates via a localizable RGB camera or a depth camera. The coordinate system of the augmented reality system can be determined on application initialization and tracked thereafter with an inertial measurement system (IMU) of the head mounted display of the augmented reality system 102.

The method 200 can further include a process to calibrate and register the surgical robot 134 for the procedure. In a step 248, the surgical robot 134 can be programmed to move the robotic image target 136 in a predetermined pattern with periodic pauses throughout the surgical field. At each of the pauses, the portion of the surgical robot 134 can be oriented so that the robotic image target 136 can be captured by a camera 138 of the augmented reality system 102 in a step 250. In a step 252, the camera 138 of the augmented reality system 102 can capture the robotic image target 136. In a step 254, each of the plurality of predetermined periodic pauses can be corresponded to a robotic coordinate. For each capture of the robotic image target 136, the corresponding pose of the robotic image target can be measured in the surgical robot 134 and augmented reality system coordinates in a step 256. These corresponding measurements can be used to determine a transformation from robotic coordinates to the augmented reality system coordinates in a step 258. This process can be automatically repeated for multiple subspaces within the surgical robot 134 reachable volume. In cases where the surgical robot 134 has tracking sensors, whether rigid or flexible, the coordinate systems of these sensors can be defined relative to the registration. For example, in the case of flexible endobronchial ultrasound (EBUS)/transrectal ultrasound (TRUS) and catheters tracked by EM or fiberoptic sensors, the coordinates can be displayed both relative to the robotic kinematic linkages and the augmented reality system, either in 3D projection with a virtual 2D live image display with HUD (Head-up display) or HDD (head-down display, as further described below).

Figure 5:
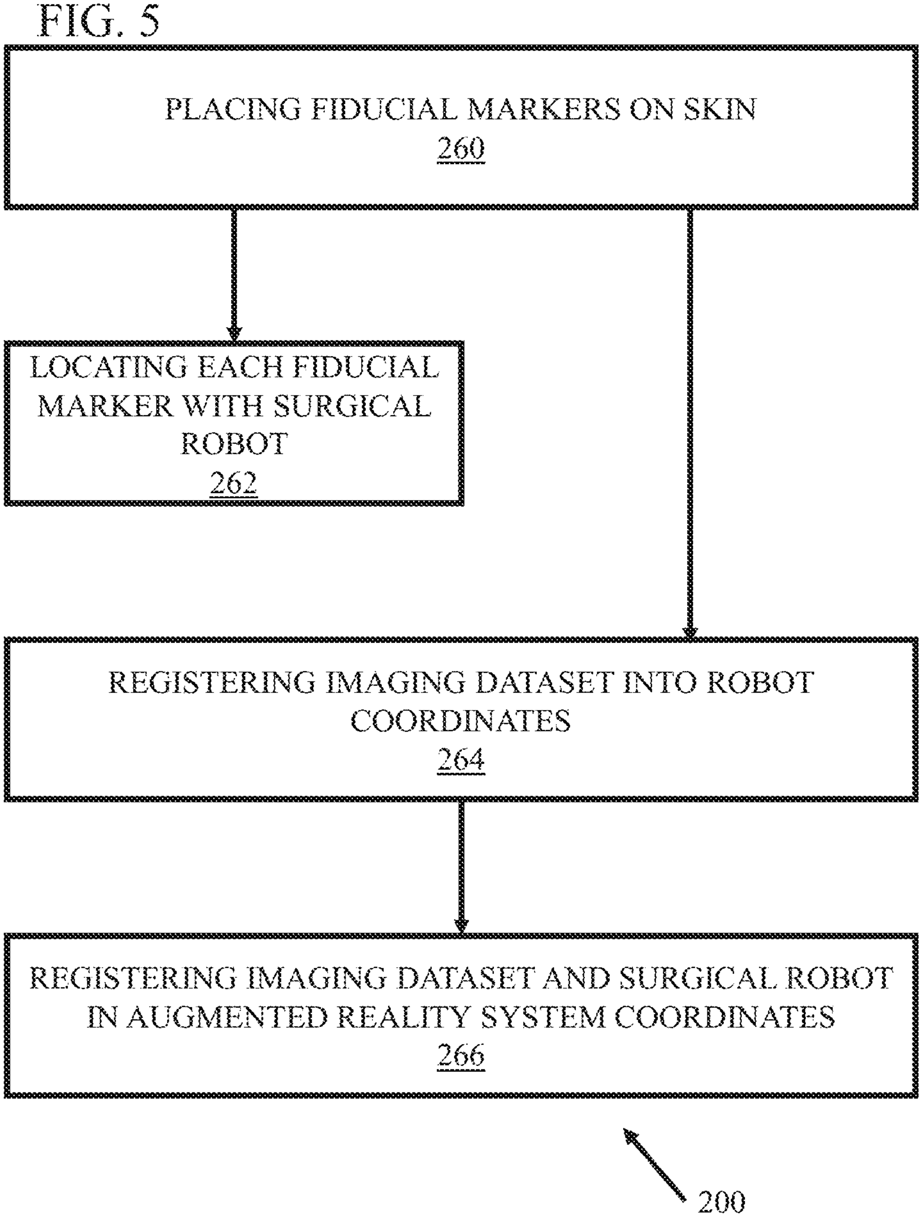
FIG. 5 is a flowchart depicting method steps for registering a pre-procedural image dataset with the augmented reality system.

With reference to FIG. 5, certain embodiments include where a pre-procedural image dataset 116 can also be registered from the imaging system 104 into augmented reality system coordinates. In a step 260, one or more fiducial markers can be placed on the skin surface for localization during imaging. Imaging based holographic projections can be used as reference to position the endoscope. During the procedure, each fiducial marker can be located with operator-controlled positioning of a calibration tool tip attached to the portion of the surgical robot 134 in a step 262. Alternatively, the imaging dataset 116 can be first registered into the robot coordinates in a step 264 and both the imaging dataset 116 and the portion of the surgical robot 134 can be registered into the head mounted display coordinates in a step 266.

After calibration and registration, endoscopic and/or surgical tool arms of the surgical robot 134 can both be located within the interventional field. The augmented reality system 102 holographic projection of the endoscopic view and the holographic representation of the tracked instrument 106 can be positioned and oriented to facilitate eye and hand coordination. The console of the medical professional can be positioned at tableside in reference to the augmented reality system 102 projection to facilitate eye-hand coordination as well as safety for the medical professional. For example, a down-the-barrel view (co-axial with the endoscopes line of site) can assist with lateral and anterior-posterior view of the surgical field to be correlated with corresponding movements of a surgical device.

XR Heads Down Display (HDD) for Live Image-Guided Procedure

Live imaging from the imaging system 104, such as CT and X-ray fluoroscopic 2D images, can be used for interventional procedures, but the live 2D images displayed on a monitor may not displayed in a position and orientation that facilitates eye-hand coordination when navigating the imaged instrument to the imaged target tissue. The head mounted display of the augmented reality system 102 can be used to holographically project the live imaging stream as a virtual 2D display monitor in approximate alignment with the image acquisition plane and, thus, in approximate alignment with the physical patient. However, in certain instances, projection of the images can be subject to occlusion and depth ambiguity. An HDD can be similar to a Heads Up Display (HUD), but can allow for specific position and orientation while militating against occlusion management and depth ambiguity. Note that although much of the value proposition for a HDD lies with interventional procedures, certain aspects of a minimally invasive surgical or traditional surgical application can be applied where live imaging is used.

It should be appreciated that the HDD projection can be correlated with the movements of the surgical instrument with the anatomical axes (e.g., right-left lateral, anterior-posterior, and caudal-cranial) as the instrument is advanced from the skin to the target and projects the live images in reference to the physical body in order to prevent occlusion and depth ambiguity. To achieve this, the imaging system coordinates (ISC) can be registered to the augmented reality system coordinates.

Live imaging 2D data of an acquisition section of the body can therefore be sent or streamed to the head mounted device of the augmented reality system 102 using a display adaptor (e.g., frame grabbing). With the coordinate registration, the head mounted display can project the live imaging of the body acquisition section approximate alignment with the physical patient during a minimally invasive surgical procedure. The live imaging can be used to guide the advancement of the imaged tracked instrument 106, typically in the image acquisition plane, since both the interventional field and the tracked instrument 106 can be imaged simultaneously for in-plane procedures (e.g., fluoroscopic procedures). For occlusion management, an additional image target 114 can be placed on the skin of the patient. The HMD camera locates the Vuforia® (Parametric Technology Corporation, Boston, Massachusetts) image target 114 and uses its location to facilitate positioning of the holographically projected HDD of live 2D CT and X-ray fluoroscopic images to meet the criteria above for eye-hand coordination and occlusion management.

For an in-plane guidance, the HDD can be projected so that it does not appear to be in the line of site between the medical professional and the physical target tissue. If HDD is projected in the line of sight, it would suggest that the 2D virtual display can be used without imaging the otherwise untracked surgical instrument as it is advanced to the physical target tissue. As such, the HDD can be minimally displaced (e.g., translated or floated) so that the projection is not in the target tissues line-of-site. The live image can be rotated by a small angle (e.g., <30 degrees) while maintaining approximate anatomic orientation of the projection to facilitate eye-hand coordination. To avoid depth ambiguity in this case, the live imaging system 104 stream can be projected above the transducer so that it is not co-projected with the physical patient. Methods to position and orient the HDD to prevent occlusion and depth ambiguity can also be applied to a stereoscopic 3D projection of 3D pre- or intra-op imaging data in world coordinate space (instead of a virtual 2D display of a live image stream). The 3D floating projection is positioned so that the line of sight does not intersect the physical patient as delineated with an image target 114 on the skin surface.

Registration of CT Data without EM Tracking and Correction for Patient Gross Motion The imaging volume dataset 120, including a multi-detector row or cone-beam CT in certain embodiments, can be used as reference in conjunction with live imaging modality such as sonography, endoscopy, or CT fluoroscopy, which can be registered in the augmented reality system coordinates by locating one or more image targets 114 in CT coordinate on the skin surface and then determining the transformation from CT to HMD coordinates. The image target 114 can have up to six-degrees of freedom with a 3D point location and a 3D orientation in the augmented reality system coordinates.

$$T_{CT\ to\ HMD} = T_{HMD}\ T_{CT}^{-1}$$

$$T_{CT\ to\ HMD}\ P_{CT\ data} = P_{CT\ in\ HMD}$$

During the registration process, augmented reality systems, such as Vuforia for example, can use a camera from a HoloLens® head-mounted device to locate physical image targets 114 in the augmented reality system coordinates. The image target 114 must have well defined corners that can be located manually or automatically during preprocedural processing of CT images. To adjust for patient gross motion during the procedure, the location and orientation of one or more image targets can be re-captured. The matrix $T_{CT\ to\ HMD}$ can be updated and applied to virtual CT objects.

Figure 6:
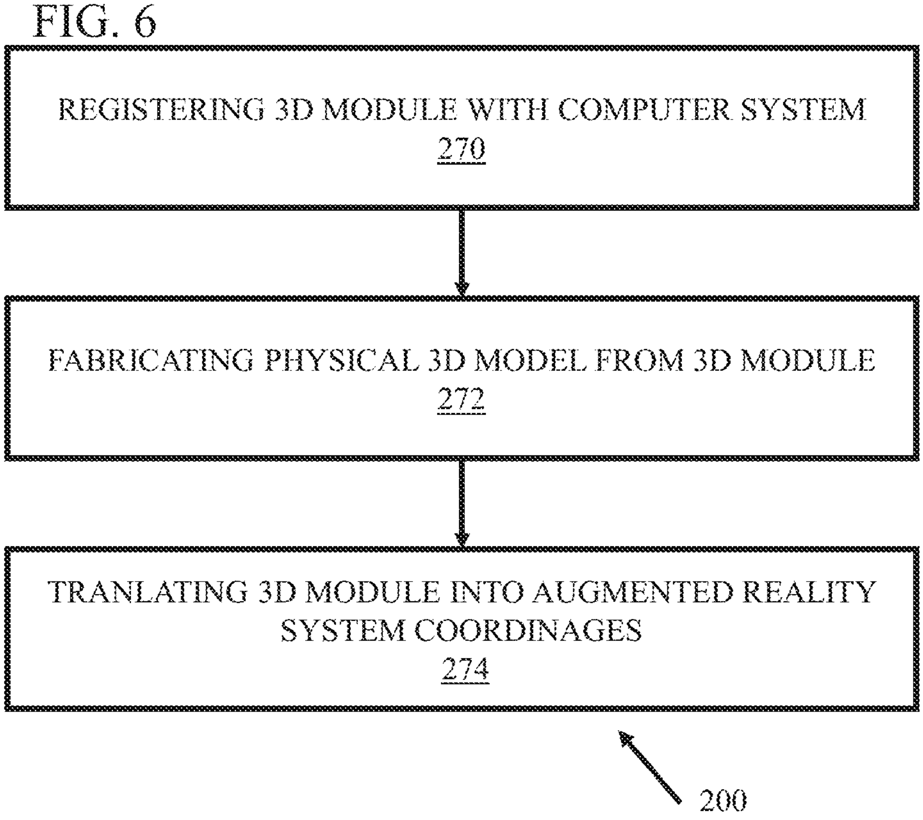
FIG. 6 is a flowchart depicting method steps for registering a 3D printed model with a holographic guidance and navigation system.

Registration of 3D Printed Model with Holographic Guidance and Navigation System With reference to FIG. 6, surgically relevant structures segmented from an image dataset 116 can be used to fabricate a physical 3D printed model and can be (concurrently or alternatively) stereoscopically projected as holograms on a head mounted display. In a step 270, a 3D module 140 of the imaging volume dataset 120 can be registered with the computer system 108. In a step 272, a physical 3D model of the 3D module 140 can be fabricated and in a step 274 the physical 3D model can be translated into the augmented reality system coordinates. This can be projected in registration with the 3D printed model before or during a surgical procedure and/or can be projected in approximated alignment with the physical patient.

The segmented structures can be transmitted to a 3D printer in STL file format. The 3D model can be printed with various materials including those that can simulate tissue deformability, such as biocompatible material such as extracellular matrix or actual printed cellular materials such as grown from stem cells in a gel matrix. The 3D printed model can include one or more contactable or sensorized fiducial marker locations that can be used to register the physical model into head mounted display coordinate system (see tracking system described herein). Alternatively, the 3D model can be printed with image targets that can be located in the augmented reality system coordinates. The same STLs file that was used to fabricate the 3D model can also be used to project holograms onto the physical patient. Patient-specific physiological information or simulations can also be projected to the 3D model.

The 3D model can be used to simulate surgical procedures either pre-procedurally or intra-procedurally with the model at table side. A surgical instrument tracking system can also be registered with the physical patient, the CT based holograms, and the 3D printed model. Components of the 3D printed model such as the skin or against vasculature can be disassembled while maintaining the anatomical structure of the remaining components during the simulation of the surgery. Note that these 3D models can both be anatomically as well as physiologically representative. Thus, imbedded sensors/fiducials printed of actual orthopedic tissue (e.g., face, hip, knee) or soft tissue (e.g., bladder, kidney, heart) devices can be paired to the guidance system for planning and implantation.

Alignment of Holographic Projection to Physical Patient (Double Alignment Portal).

The perception of registration of a holographic projections to the physical world can be affected by the viewing angle and the ability of the head mounted display to stabilize the hologram with head movements. In instances where it is useful to align the hologram to the physical world, methods can be used to control the viewing angle while providing guidance and visualization to the operator to complete the task. An example includes a projection of a deformable skin surface hologram to the physical skin surface. The deformation of the tissue can be adjusted to match the static holographic projection derived from imaging, but this should be performed at a reproducible viewing angle which can then also be used to complete the procedure. Controlling and restraining the viewing angle during projection of a hologram to its corresponding physical structure is referred to as a (single) alignment portal.

An untracked physical instrument would have depth ambiguity in holographic projection to the physical body. This can be addressed by aligning the center axis of a surgical instrument when the viewing direction is along the optical axis of the stereoscopic projection. A cylindrical hologram can be used to plan this alignment in reference to the anatomical structures of interest for planned alignment of the center axis of a surgical instrument. For this, the system can provide feedback when operator's line of sight is aligned with the cylindrical hologram (e.g., down-the-barrel view) without relying on depth cues that can be ambiguous when projecting holograms with see through lenses. The holographic cylinder can be aligned with the operator's visual axis. Criteria for establishing the down-the-barrel view can include eye-tracking and head mounted display line-of-sights having a sufficiently low angle relative to the alignment cylinder. One or more surgical points of interest on a directly exposed anatomical surface can be located with one or more holographic projections. An image target can be placed relative to one or more anatomical structures and the holographic projection can be registered in relationship to said structures. A calibration step can be used to ensure alignment of the virtual and physical representations of the image target, thereby aligning nearby structures. Controlling and restraining the projection viewing angle during projection of a hologram to its corresponding physical structure and projection of an un-tracked surgical device is referred to as a double alignment portal.

Methods to Determine Electromagnetic to Augmented Reality System Transformation such that Electromagnetic Devices are Tracked Relative to Physical Patient.

Systems and methods of the present disclosure can be utilized to determine an electromagnetic to augmented reality system transformation with electromagnetic devices tracked to a physical location for a patient. For example, a stationary electromagnetic generator can be utilized to register the electromagnetic data relative to the physical location of the patient. In other embodiments, a combination marker or a six degree of freedom sensor can be utilized to perform the electromagnetic to augmented reality system transformation, for example. Desirably, these embodiments allow a practitioner to employ the system where fiducial markers are not readily available.

Treatment Using Ablation Zones

Figure 7:
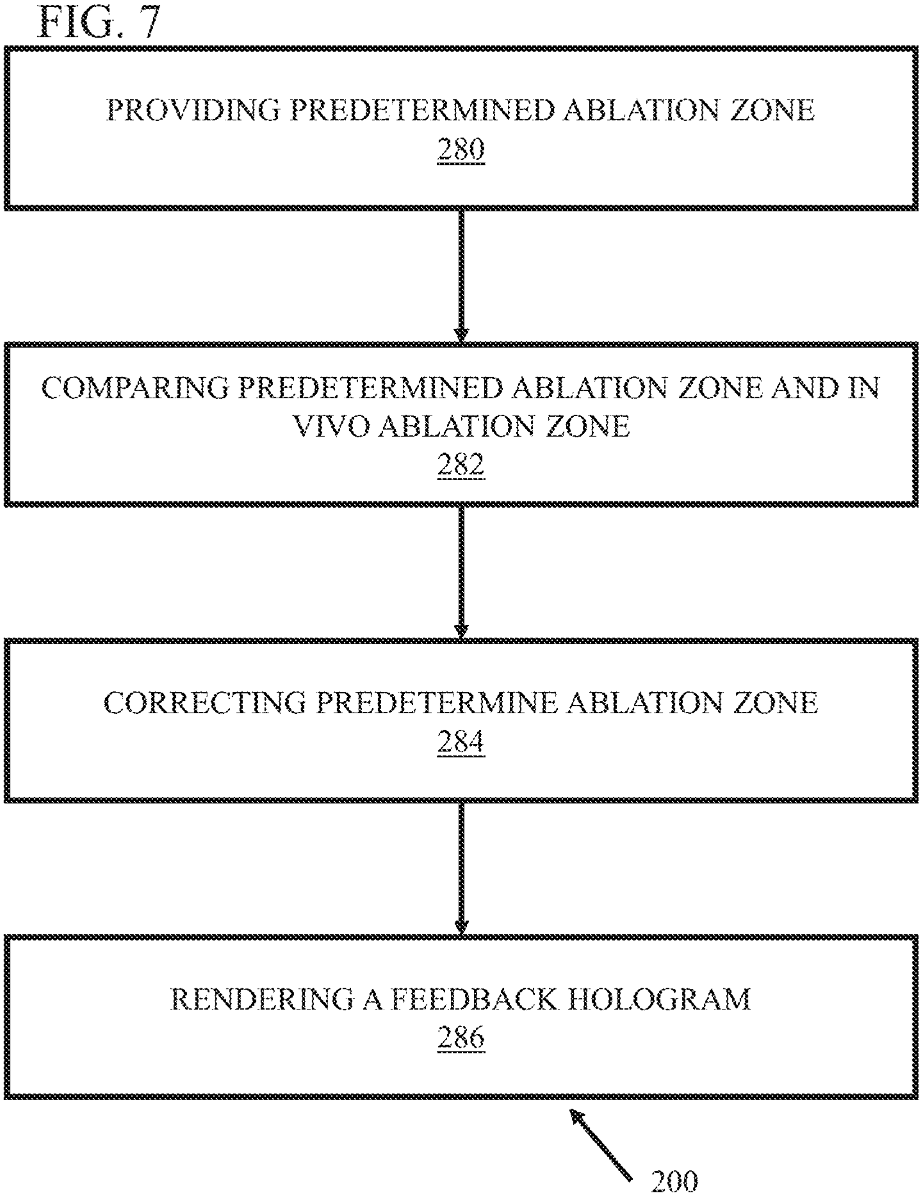
FIG. 7 is a flowchart depicting method steps for determining an in vivo ablation zone.

With reference to FIG. 7, certain embodiments include where the method 200 can include a step 280 of providing a predetermined ablation zone. The predetermined ablation zone can be selected and determined preoperatively by the medical professional. In a step 282, the predetermined ablation zone and the in vivo ablation zone can be compared during the procedure. The method can include a step 284 of correcting the predetermined zone based on the in vivo ablation zone to allow for a more accurate ablation in real time. In this way, the method can include a step 286 of rendering, by the augmented reality system 102, a feedback hologram once the ablation has occurred to identify if additional intervention is required.

EXAMPLES

Example applications of the present technology are provided with reference to the several figures enclosed herewith. Operation of the system provided by the present disclosure can be described by way of example. In particular, the system is useful in applications where the system can be expanded and interfaced in situations to afford the user better decision-making capabilities. Some examples of these are provided in the following applications.

Application 1: Urology

Prostate cancer is the second leading cause of cancer death in American males with 1 in 8 to be diagnosed in his lifetime. More than 1 million prostate biopsies are performed each year in the United States. A clinical diagnosis cannot be made until a biopsy is performed and a pathologist reviews the histological results. However, repeat biopsies are common if sufficient samples were not retrieved or if the samples have not been dispersed enough throughout various regions of the prostate. False-negative rates for initial biopsies are as high as 20%-30%. Moreover, complication rates for a 24-sample biopsy are as high as 57%.

Typically, a transrectal ultrasound (TRUS) probe can be inserted into the rectum to visualize the prostate. Alternatively, a transperineal approach may be used. A pre-procedural MRI may also be obtained and fused to the ultrasound image to guide the biopsy procedure. The combination of MRI and TRUS is becoming more common in prostate biopsy. Adding EM-tracking of a TRUS probe during a prostate biopsy along with an EM-tracked biopsy needle and registered can provide improved navigation and depth perception visualizing the live ultrasound feed within the spatial context of the procedural workspace. The pre-operative MRI images can be segmented and registered along with the two tracked devices leveraging the unique registration capabilities of the present system.

Recently, general practice has adopted a higher number of biopsy cores to increase the likelihood of detection. However, without the integration of MRI, this can also increase the chance of finding small, indolent cancers instead of clinically relevant tumors. Planned biopsy cores can be placed in spatial alignment to an MRI segmented prostate preoperatively. These planned cores can then be referenced and adjusted to match the TRUS-imaged anatomy by adjusting the registration of the MRI to correlate with the boundary of the prostate. Typically, each core is placed 5 mm apart which can be algorithmically arranged and optimized and projected within HMD world space. These planned trajectories can be tweaked to ensure completeness of coverage to reduce repeat biopsies. Each biopsy core can be labeled, and the eventual resulting histologic data can be tied to the specific core volume and coordinates from which it was taken and uploaded to the patient's medical record. This data is then saved for future surgical interventions such as resection, if deemed necessary based on biopsy findings.

Data can be played back in 3D space for "ghost" feedback during a procedure which allows the physician to playback their previous procedure in real-time, holographically during the procedure. The spatially registered 3D holographic representation of segmented MRI, ultrasound image, and tracked needles can be projected at the appropriate position of the prostate and at an orientation that facilitates eye-hand coordination when deploying the needle in either a transrectal or a transperineal approach. The MRI data can be textured to show regions of the prostate that are more likely to be malignant to facilitate more diagnostic accuracy of the biopsy. This AR system for prostate can also be used for treatment such as the placement of radioactive brachytherapy seeds or when performing prostate lumpectomy. The system can reformat the MRI images to be co-planar to the transrectal ultrasound images.

These planned biopsy cores can be looked at retrospectively as well to determine placement error and the correlation to successful biopsy outcomes to reduce unnecessary repeat biopsies. Post-operatively, results from the biopsy cores can be used to map the prostate into regions delineating healthy tissue vs cancerous tissue.

The registration methods described herein related to the 3D printed options can also be employed in relation to the urology treatments. For example, pluripotent stem cells have been used to grow a donor bladder and have been implanted in humans lasting several years.

Application 2: Breast

Breast cancer therapy can include the implantation of markers prior to lumpectomy or ablation due to highly malleable tissue. These markers can be registered within the holographic coordinate system and thus tracked during the procedure. For minimally invasive surgery, the tumor may or may not be resected. The void can be navigated under ultrasound guidance displayed in the HMD relative to the void and/or markers if present. Then the pre-procedurally planned ablation zones can be to the tracked ablation margin with ice ball under ultrasound, MRI, or similar. This can be analyzed and addressed during or after the procedure. Dye may be able to track cancerous cells migrating to lymph nodes and this can be illustrated in a registered hologram. If the tumor is removed, the removal, physical aspects, and location of the tumor can be tagged for later tracking in this same coordinate system. It should be appreciated that with any ablation modality discussed herein, multiple probes can be registered relative to the other. The system can add and display ellipsoids overlapping. However, by building in the proximity of these ablation zones and gradients of energy/thermal/electrical field the overlap of ablation zones cover a different volume. Furthermore, these multiple probes can combine separately with generated unipolar fields, however, can intentionally combine via bipolar and/or biphasic means so that their coordinated phases can combine into a kill zone that is more than the "sum of their parts".

A lumpectomy device can be tracked into the former tumor void and radioactive seed positioning and radiation delivery can be tracked by location. The radiation delivery data can be visualized in 3D and compared to the expected margin and adjusted as needed during the procedure. This procedure can be performed outside of a hospital so the pre-, intra-, and postoperative procedures, augmented reality aspects, including conversations with other experts, can be shared remotely and locally.

When using a three-dimensional data set for image guidance acquired prior to the procedure, a common problem is the intra-op deformation anatomical structures and of the target tissue relative to the static pre-op data set. When a deformation of the tissue occurs then the static data set combined with virtual representation of track devices can be inaccurate due to the misregistration of the physically deformed tissue to the static data set. A method to control the deformation of target tissue can be to acquire the imaging data set, such as magnetic resonance imaging, in a controlled fashion such that the targeted tissue is approximately shaped the same as during the image acquisition (e.g., supine) as it is during the procedure (e.g., supine). If the patient is positioned and oriented similarly during the image acquisition and the surgical procedure, then the soft tissue structures would not be as deformed as if the patient were positioned at a different orientation (e.g., prone) during image acquisition.

Additional methods can be used to control the shape of the target tissue relative to the image acquisition. The skin surface segmented from the imaging data set can be projected to the physical tissue to verify and adjust the target tissue shape such that it is sufficiently similar to the shape it was during the acquisition of the imaging data. During shape adjustment, projection of the segmented skin hologram to the physical surface can be in a controlled viewing angle as described and the alignment portal. This would militate against variations in the perception of alignment of the skin hologram to the physical surface based on variations in viewing angle. The ultrasound probe pressed on to the physical skin surface can also cause deformation of the target tissue. Methods can be used to minimize this deformation such as extra acoustic gel on the skin surface and an optional use of an ultrasound probe holder. This deformation can be detected and mitigated by comparing the position of the tracked physical ultrasound probe surface to the holographic skin surface segmented from the imaging data set, whereby the tracked probe and holographic skin surface have been registered into HMD coordinates. Feedback can be provided to the operator regarding the extent the tracked physical probe is below or medial to the segmented skin surface.

Application 3: Pulmonology/Lung

Endobronchial ultrasound (EBUS) bronchoscopy is a procedure used to diagnose different types of lung disorders, including inflammation, infections or cancer. Performed by a pulmonologist, EBUS bronchoscopy uses a flexible tube that goes through the patient's mouth and into the windpipe and lungs. Similar to, though smaller than, the device used during a colonoscopy, the EBUS scope can have a video camera with an ultrasound probe attached to create a local image of the lungs and nearby lymph nodes in order to accurately locate and evaluate areas seen on pre-procedure radiographs or CT or scans that need a closer look. As can be seen by the overview of procedural steps, EBUS and/or robotic EBUS can be registered to the holographic coordinate system (i.e., head mounted display or world) and tracking via US, EM, fiberoptic, or other sensors. Unique EBUS characteristics that can be modeled and registered in holographic coordinates, such as the shape of the balloon and echogenic markers. HMD/HDD location flexibility affords the physician the ability to use multiple preferred locations and move intraprocedurally as necessary.

Adjacent structures like the vocal cords can be visualized and avoided with planning and defined 3D trajectory. Target trajectories can be planned and relatively tracked/visualized so that the EBUS can be optimally flexed and rotated. The needle tip can be tracked during approach and doppler view in 3D to confirm target localization. The needle tip can be tracked during the multiple manipulations to ensure optimal biopsy. Note that flexible catheter can be similarly used to ablate targets in much of the same way. This can be tracked with EM or fiberoptic. The sector of the EBUS transducer can be delineated with holographic line segments. Also, referencing back to FIG. 1 and the methods it is common to have respiratory phase motion accounted for as well as robotics.

CT-to-body divergence is a well know problem in CT guided bronchoscopy whereby the physical lung structures are not in alignment with the pre procedural multidetector CT used to plan the procedure for example to biopsy peripheral pulmonary nodules.

Augmented reality can be used to assess this divergence using intra operative cone-beam CT to assess the current stationary body positioning and shape and then compare this with the preprocedural multidetector row CT. To compare the multidetector row CT with the intra-op cone-beam CT, these two imaging results can be co-registered and co-projected (using volume rendering or segmented results) to the physical patient by co-registering them to an anatomical structure such as the sternum which is relatively invariant to ventilation and respiratory motion. A Vuforia image target can be precisely placed on the physical sternum in reference to anatomical landmarks, such as the jugular notch and the xiphoid process, located physically and in both the image data sets. The nodule can also be located in both imaging data sets. This enables the Euclidian distance to be computed between the center of the virtual targeted nodule in the two imaging modalities. The ventilation and or body position can then be adjusted, and the cone beam CT be repeated to decrease the divergence relative to the planned multi detector row CT. Live fluoroscopy, which has a lower radiation dose relative to CBCT, streamed as a virtual display monitor on the HMD can also be companioned with a reprojection of the pre-op MDCT data set to adjust the ventilation and body position. For this, the reprojection of MDCT is performed using C-arm camera geometry (such as x-ray source to detector distance) and C-arm pose.

Application 4: Pancreas/Colorectal

As identified herein, applications are not limited to percutaneous procedures and the present technology can be applied to minimally invasive or surgical procedures in practice. The below example for pancreatic cancer is an example that can significantly benefit from application of the HDD to plan adjacent targets and visualize surgical boundaries, where the pancreas anatomy provides an example of a complex procedure with adjacent structures and planned surgical boundaries. Other therapies with ablation applications such as radiofrequency ablation (RFA), microwave ablation (MWA), pulsed electrical field via irreversible electroporation (PEF) can incorporate and benefit from the present technology along with 3D printing registration visualization. Note that Whipple procedure require an innate understanding of the vascularization that has taken place due to the cancer, then subsequently needs to be reconstructed after resection. The pancreas is very deep in the body cavity so all the layers, connective tissue, adjacent structures that need to be navigated is important.

Some practitioners prefer microwave ablation (MWA) since it is less susceptible to heat sink and the difference can be planned for in the holographic model. If, for example, a practitioner plans to use cryoablation, modeling and registration of the ablation zone can be performed differently, and ice ball formation can be monitored with ultrasound or CT. If one used PEF, the present technology can model the electrical field and adjust accordingly, and display data differently since PEF takes much less time. Yet another therapy can include ultrasound guided alcohol injection/ablation, which can also be applied using the present technology. In this way, the practitioner can still plan and track subsequent procedures and ascertain effectiveness in treating the center of the tumor and add external radiotherapy, as necessary. Multiple modalities can be considered in combination depending on the need such as adjacent structures.

For intraprocedural planning complex anatomy can be 3D stereoscopical holographically projected and floated in proximity or above the patient in a HMD heads down display as described previously. The materials, transparency/opacity, and 3D lighting can be adjusted such that overlapping and enclosed on structures can be adequately visualized to assist the surgeon during the procedure. Multiple imaging data sets, such as pre- and post-radiation therapy, can be shown side-by-side (vertical or horizontal). Vascular structures can be segmented from high resolution imaging images to project holographic angiography (vascular) roadmap, which can be scaled-up and oriented in correlation with the physical patient to assist during complex surgery.

Application 5: Liver

Radio frequency ablation (RFA), microwave ablation (MWA), pulsed electrical field via irreversible electroporation (PEF), percutaneous ethanol injection (PEI), embolization therapy, etc. can all potentially be used for liver therapy. Unlike an MWA antenna, some of the RFA probe has several small tines/wires that extend/retract from the needle to burn that each be tracked much like a transcatheter heart valve or stent can be registered at multiple points. Additionally, one can incorporate data like 3D ultrasound modeling, registration, planning with the holographic registration and display to visualize and display ablation margin data overlaid on the patient. There is also a transient effect to the ablation, for example a MWA ablation grows after 24 hrs so this system can be used at multiple time points for comparison so the registration at those time points to accurately compare is needed. Planned and resulting ablation zones will be recorded pre-ablation and post-ablation with axial images of the tumor, respectively, and registered to compare and quantify agreement in terms of (1) volume, (2) surface area, (3) percent volume beyond 5 mm tumor margin, and (4) percent volume of tumor not included, as well as (5) an intersection-over-union metric.

Application 6: Planning Ablation Zones

Ablation modalities such as microwave, cryogenic and pulsed electric field, are estimated empirically by applying the energy to an animal or physics model, which does not always provide accurate estimation of the ablation zones in human tissue. If the planned and resulting ablation zones are recorded, then these can be compared in terms of volume and shape of the ablation zones. The planned and resulting zone can be recorded relative to the imaged tumor and then the zones can be compared by registering the image target tumor. Comparing the pre-planned and resulting ablation zones provides input to a method to update estimations for the planned ablation zones. If the resulting ablation zone is consistently larger than the estimated planned ablation zone, for example, then the planned ablation zone size can be increased for future cases. In the long run, the planned ablation zone can be more consistent with the resulting ablation zone, which can provide advantages when positioning the probes and antennas with 3D guidance and navigation, and thereby provide better coverage of the tumor, less co-lateral damage to nearby structures, and a better outcome for the treatment.

Methods described herein for registration and visualization can be combined when used for an application. As one example, registration without fiducial markers by using the skin hologram segmented from imaging to physical skin by attaching the skin hologram to a tracked sensor can be used for breast and liver applications in combination with method for EM-to-HMD and the alignment portal deformation As another example, 3D stereoscopy projection of 3D holograms floating above the physical patient can be combined with use of the HDD for live imaging, where both projections can benefit from methods to enhance eye-hand coordination and prevent occlusion and depth ambiguity.

Another example, after registration of tracking and imaging data to the HMD coordinates, the CT or MRI multiplanar images reformatted from the DICOM data volume to be co-planar with the tracked ultrasound image in HMD coordinates can be used to output images of the tumor with planned ablation zone for comparison with the resulting ablation zone. The output images can be in the standard anatomical orientation such as axial, sagittal, and coronal. The system can provide angular feedback to help the operator generate the anatomical planes.

Example applications are provided so that this disclosure will be thorough, and will fully convey the scope to those who are skilled in the art. Numerous specific details are set forth such as applications of specific components, devices, and methods, to provide a thorough understanding of embodiments of the present disclosure. It will be apparent to those skilled in the art that specific details need not be employed, that application embodiments may be embodied in many different forms, and that neither should be construed to limit the scope of the disclosure. In some application embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A method for registration of anatomy of a patient using augmented reality for a procedure on a patient, comprising:

providing a system including:

an augmented reality system configured to display an augmented representation of an anatomical feature of the patient in an augmented reality;

an imaging system configured to image the anatomical feature of the patient and generate an imaging dataset without the use of fiducial sensors;

a tracked instrument configured to be used during the procedure and to generate a tracked instrument dataset; and a computer system in communication with the augmented reality system, the imaging system, and the tracked instrument;

positioning the tracked instrument in a first axial plane and collecting, from the tracked instrument, the tracked instrument dataset;

positioning the imaging system in a second axial plane and collecting, from the imaging system, the imaging dataset;

identifying an internal landmark of the patient with both the tracked instrument and the imaging system;

aligning the first axial plane and the second axial plane based on the internal landmark identified;

generating, by the computer system, an imaging volume dataset based on the first axial plane and the second axial plane in 3D coordinates;

registering, by the computer system, the imaging volume dataset with the augmented reality system;

rendering the imaging volume dataset into an imaging volume hologram;

projecting, by the augmented reality system, the imaging volume hologram; and registering a surgical robot for the procedure, including:

attaching a robotic image target to a portion of the surgical robot at a predetermined position and a predetermined orientation;

aligning the robotic image target within 3D cartesian coordinates; and localizing the robotic image target with augmented reality system coordinates;

calibrating and registering the surgical robot for the procedure, including:

programming the surgical robot to move the robotic image target in a predetermined pattern, wherein the predetermined pattern includes a plurality of predetermined periodic pauses;

orienting the portion of the surgical robot that includes the robotic image target at each of the plurality of predetermined periodic pauses;

capturing, by a camera of the augmented reality system, the robotic image target at each of the plurality of predetermined periodic pauses;

corresponding each of the plurality of predetermined periodic pauses to a robotic coordinate;

measuring, in a robotic coordinate system, a position of the robotic image target; and determining a transformation from the robotic coordinate system to the augmented reality system coordinates.

2. The method of claim 1, wherein the first axial plane and the second axial plane are aligned to be orthogonal.

3. The method of claim 1, wherein the first axial plane and the second axial plane are aligned to be oblique.

4. The method of claim 1, wherein the first axial plane and the second axial plane are aligned to be coplanar.

5. The method of claim 1, further including steps of:

locating sagittal midline on the patient; and rotating the imaging volume hologram such that a holographic sagittal midline of the imaging volume hologram and sagittal midline on the patient are congruent.

6. The method of claim 1, further including steps of:

segmenting a skin surface image from the imaging dataset, thereby creating skin surface imaging data;

aligning, by a tracking sensor, the skin surface image data to the patient; and registering the skin surface image data to the imaging dataset and the tracked instrument dataset.

7. The method of claim 1, wherein the tracked instrument dataset includes an electromagnetic dataset.

8. The method of claim 1, wherein the step of collecting the imaging dataset further includes steps of:

positioning an image target on a skin surface of the patient; and locating the image target with a calibration tip coupled to the portion of the surgical robot.

9. The method of claim 8, wherein the step of registering the imaging volume dataset with the augmented reality system further includes steps of:

registering the imaging volume dataset into the robotic coordinate system; and translating the imaging volume dataset from the robotic coordinate system to the augmented reality system coordinates.

10. The method of claim 1, wherein the augmented reality system includes a head down display for projecting the imaging volume hologram.

11. The method of claim 1, further including steps of:

providing a predetermined ablation zone; and correcting the predetermined ablation zone based on the imaging volume hologram.

12. The method of claim 1, further including a step of registering a 3D model of the imaging volume dataset.

13. The method of claim 12, wherein the step of registering a 3D model of the imaging volume dataset includes a step of fabricating a physical 3D model.

14. The method of claim 13, wherein the physical 3D model includes an image target location for registering the physical 3D model into augmented reality coordinates.

15. A system for registration of an anatomical feature of a patient using augmented reality, comprising:

an imaging system configured to image the anatomical feature of the patient and generate an imaging dataset;

a tracked instrument configured to generate a tracked instrument dataset;

an augmented reality system configured to display an imaging volume hologram of the anatomical feature of the patient in augmented reality;

a surgical robot having a robotic image target attached to a portion of the surgical robot at a predetermined position and a predetermined orientation; and a computer system in communication with the augmented reality system, the imaging system, and the tracked instrument, the computer system configured to:

generate an imaging volume dataset based on a first axial plane and a second axial plane;

render the imaging volume dataset into the imaging volume hologram;

project the image volume hologram in an augmented reality environment of the augmented reality system;

align the robotic image target within 3D Cartesian coordinates;

localize the robotic image target with augmented reality system coordinates;

program the surgical robot to move the robotic image target in a predetermined pattern, wherein the predetermined pattern includes a plurality of predetermined periodic pauses;

orient the portion of the surgical robot that includes the robotic image target at each of the plurality of predetermined periodic pauses;

capture, by a camera of the augmented reality system, the robotic image target at each of the plurality of predetermined periodic pauses;

correspond each of the plurality of predetermined periodic pauses to a robotic coordinate;

measure, in a robotic coordinate system, a position of the robotic image target; and determine a transformation from the robotic coordinate system to the augmented reality system coordinates.

16. The system of claim 15, wherein the tracked instrument includes at least one of a needle and an electromagnetically tracked ultrasound.

17. The system of claim 15, wherein the imaging system includes at least one of a computed tomography (CT) system, a fluoroscopy system, positron emission computed tomography, magnetic resonance imaging (MRI) system, and an ultrasound (US) system.

18. The system of claim 15, wherein the augmented reality system includes a head down display.

* * * * *